United States Patent [19]

Thacker et al.

[11] Patent Number: 5,106,634

[45] Date of Patent: * Apr. 21, 1992

[54] PROCESS FOR THE CO-PRODUCTION OF ETHANOL AND AN IMPROVED HUMAN FOOD PRODUCT FROM CEREAL GRAINS

[75] Inventors: Ray S. Thacker, Clovis, N. Mex.; Bill A. Dodgin, Amarillo, Tex.

[73] Assignee: Clovis Grain Processing, Ltd., Amarillo, Tex.

[*] Notice: The portion of the term of this patent subsequent to Oct. 29, 2008 has been disclaimed.

[21] Appl. No.: 575,214

[22] Filed: Aug. 30, 1990

Related U.S. Application Data

[63] Continuation-in-part of Ser. No. 405,463, Sep. 11, 1989, Pat. No. 5,061,497.

[51] Int. Cl.$^5$ ............................................. C12F 3/10
[52] U.S. Cl. .................................... 426/31; 426/44; 426/49; 426/53; 426/459; 426/460; 426/615; 426/618; 435/161
[58] Field of Search ............... 426/31, 44, 49, 53, 426/459, 460, 615, 618; 435/161

[56] References Cited

U.S. PATENT DOCUMENTS

| | | | |
|---|---|---|---|
| 1,363,193 | 12/1920 | Coombs | 426/28 |
| 1,543,458 | 6/1925 | Takamine | 426/28 |
| 2,284,416 | 7/1942 | Fine et al. | 426/28 |
| 2,555,235 | 5/1951 | Huzenlaub et al. | 99/80 |
| 2,853,388 | 0/0000 | Kiely et al. | |
| 3,212,902 | 10/1965 | Bavisotto | 426/31 |
| 3,950,543 | 4/1976 | Buffa et al. | 426/18 |
| 4,254,150 | 3/1981 | Fritze et al. | 426/18 |
| 4,341,805 | 7/1982 | Chaudhary | 426/481 |
| 4,374,860 | 2/1983 | Gasser | 426/28 |
| 4,435,430 | 3/1984 | Fulger et al. | 426/18 |
| 4,617,270 | 10/1986 | Anderson et al. | 435/161 |
| 4,810,647 | 3/1989 | Monceaux et al. | 435/106 |
| 4,828,846 | 6/1989 | Rasco et al. | 426/18 |
| 4,834,989 | 5/1989 | Bolles et al. | 426/28 |

FOREIGN PATENT DOCUMENTS 2940859 4/1981 Fed. Rep. of Germany.

OTHER PUBLICATIONS

Prentice et al, High Fiber Cookies Containing Brewers Spent Grain, Cereal Chemistry, vol. 55, #5, pp. 712-721, 1978.

Bookwalter et al., Cereal Chemistry, vol. 61, No. 6, 1984, pp. 509-513.

Tsen et al., Journal of Food Science, vol. 47, pp. 684-685, 1982.

Kirk-Othmer, Encycl. of Chem. Tech., vol. 3, pp. 697-699; pp. 704-710; and p. 722.

*Primary Examiner*—Donald E. Czaja
*Assistant Examiner*—Evan Federman
*Attorney, Agent, or Firm*—Alec H. Horn

[57] ABSTRACT

A process for producing a novel cereal grain food product is disclosed. This novel food product is high in fiber and protein with a complex sugars coating that renders the product good-tasting and suitable for human consumption. This process involves the enzymatic conversion and removal of starch from the grain. The converted grain is separated from its liquor before the liquor is fermented to produce ethanol. The food product may be incorporated into baked goods, drinks, breakfast cereals and the like or eaten "as is."

39 Claims, No Drawings

PROCESS FOR THE CO-PRODUCTION OF ETHANOL AND AN IMPROVED HUMAN FOOD PRODUCT FROM CEREAL GRAINS

This application is a continuation-in-part of co-pending U.S. patent application Ser. No. 405,463, filed Sept. 11, 1989 now U.S. Pat. No. 5,061,497.

The products and process of the present invention relate to recovering human food value from the residues remaining after starch containing cereals and the like have been converted to sugar during the production of ethanol. More particularly, the invention relates to compatibly producing an industrial grade ethanol and a high-fiber, high-protein food product which is suitable for human food use.

BACKGROUND OF THE INVENTION

Perhaps one of the oldest industrial chemical processes is the production of ethanol from starchy agricultural products using natural enzymes and yeast. This process has been utilized by brewers and distillers for centuries and is currently of special commercial interest in the well-known industrial production of fuel grade alcohol from grain.

It is well known that brewers of beer preferably use malted barley. One desireable difference between barley and other common cereals is that the husk adheres to the kernel after threshing. This feature makes the process of malting and subsequent extraction of the wort much easier than with wheat or other grains.

In the beer-making process, great care is taken to make sure that crushing occurs over the whole length of the kernel. This preserves the husk almost intact to aid in filtration. A careful balance between extraction efficiency and filtration efficiency must be met.

Ancient experience teaches that if the husks of the malted barley are crushed too finely, leaching of bitter materials from the husks imparts undesirable flavor and shortened shelf life to the beer. On the other hand, beer produced entirely from dehusked malt has a very unsatisfactory flavor. Accordingly, the husks of the malted barley are a necessary part of the brewers' art.

Prior to fermentation, the brewer separates the sweet wort from the spent grains utilizing the coarse husks as a filter material. This filtering should take place rapidly with substantially all sugars washed out of the spent grains.

The very process steps necessary to produce fine beers, result in spent grain having unacceptable organoleptic characteristics. The necessity of leaving the husk of the malted barley intact results in the spent grains being course and rough. The required chemical changes during malting which gives the beer satisfactory flavor, leaves the husk bitter and organoleptically unacceptable for human food use.

A further requirement of good beer-making practice, which has detrimental effects on spent grains as a human food, is a result of the changes made in the proteins in the mash. The malted barley also contains protein-degrading enzymes, notably protease, which converts proteins into peptides and amino acids during mash digestion. These nitrogeneous peptides and amino acids are soluble and are filtered away from the spent grains to be used in the wort. This generally results in lower protein levels in the spent grains. These nitrogenous materials are later precipitated from the fermented beer and added back to the spent grains, which increases bitterness because of exposure to the fermentation process.

Currently, corn is the most popular grain used to commercially manufacture fuel alcohol. The process typically involves a two-stage enzymatic conversion of starch to sugar, followed by fermentation and then distillation to recover alcohol and carbon dioxide. Manufacturers typically dry the grain residue and sell the dried product, commonly called "Distillers' Dried Grains," as an animal feed or as a component of animal feed products. The soluble portion of the residue is often dried separately.

At the present time, wheat or other grains are not an economical choice as a fermentation substrate unless the spent grain can be sold for a higher price as human food rather than animal feed. Wheat residues are generally higher in protein, lysine, and threonine than corn residues. The process for manufacturing alcohol from wheat is very similar to that of corn.

Utilization of alcohol production residues have received little application beyond use in animal feeds. A major problem with distillers' grain residue is that it possesses a distinct odor and taste which negatively affects acceptability even for use in animal feed. Many attempts have been made throughout the years to find acceptable human food grade applications for Distillers' Dried Grains and Brewers Spent Grains, but without success. For a thorough discussion of the use of Distillers' Dried and Brewers' Spent Grains in human food, see U.S. Pat. No. 4,828,846 to Rasco, et. al. which is hereby incorporated by reference.

Rasco, et. al. teaches that the unpleasant taste and odor of Distillers' Dried Grains may be masked or reduced by the careful adjustment of pH by suitable acids and bases during starch conversion and before drying. The spent grains so treated may be used in human food products. Although an improvement over the dried grains of the typical alcohol production process, these products have proven only marginally successful. The grain products so produced still have an unacceptable taste and must be used at low flour substitution levels.

SUMMARY OF INVENTION

In the product of the present invention a high fiber, high protein food product is produced which is organoleptically suitable for human consumption. This food product comprises milled starch-bearing cereal grains which have had 90 to 100% of the starch enzymatically converted. These converted cereal grains have a protein content on a dry matter basis substantially between 17 to 35% by weight. These converted grains also have a total dietary fiber content on a dry matter basis substantially between 30 to 70% by weight and a nitrogen-free extract content on a dry matter basis less than 40%. Further, the grains have a coating of residual sugars thereon from the enzymatic conversion of starch which is 4 to 30% by weight on a dry matter basis.

In the process of the present invention a high protein, high fiber food product which is organoleptically suitable for human consumption is produced from starch-bearing cereal grains. The process comprises the steps of suspending the cereal grains in a selected amount of water to form an aqueous slurry, heating the slurry, liquifying and hydrolyzing a selected amount of the starch and separating the grain solids fraction from the aqueous fraction to produce a substantially solids-free aqueous sugars fraction and solids cake. In this process, the aqueous slurry is heated sufficiently to at least partially gelatinize the starch.

During the liquifying and hydrolyzing of the starch with enzymes, the selected amount of starch hydrolyzed is between 90 to 100% which produces a grain mixture to be separated. The aqueous sugars fraction of this mixture has a selected sugars content. The sugars in the sugars fraction contains less than 5% glucose.

The grain solids fraction of the grain mixture is separated from the aqueous sugars fraction of the mixture to produce a substantially solids-free aqueous sugars fraction and a grain solids cake. The grain solids cake is dried in the presence of a sufficient quantity of the aqueous sugars fraction to produce a food product having a coating thereon of residual sugars from the enzymatic conversion of starch substantially between 4 to 30% by weight on a dry matter basis.

The food products of the present invention also include baked goods made with cereal flour containing the above described high fiber, high protein food product in an amount less than substantially 50% by weight of the cereal flour. Other food products of the present invention comprise either ready-to-eat or cooked cereal including the above described high fiber, high protein food product. Yet other food products of the present invention include high fiber, high protein food products made by the processes above described.

It is an object of the present invention to increase the value of the products resulting from the production of grain alcohol by simultaneously producing a higher value added spent grain product than heretofore possible.

It is another object of the present invention to produce an organoleptically acceptable grain product which is high in fiber an protein during the production of grain alcohol.

It is yet another object of the present invention to produce a grain product from grains specifically blended to produce an ideal soluble fiber to insoluble fiber ratio while maintaining highly acceptable flavor.

It is yet another object of the present invention to produce a grain product having sufficient flavor to be consumed "as is" or as a partial substitute for flour.

It is yet another object of the present invention to produce a human grade food product of highest quality while simultaneously producing industrial grade alcohol without the requirement of a complete food grade production system.

It is yet another object of the present invention to produce a human food product of highest quality while simultaneously producing food-grade alcohol.

DISCUSSION OF THE BEST MODE OF THE INVENTION

In a preferred process of the present invention high quality grain is properly cleaned and aspirated to remove any foreign material both larger and smaller than the grain kernel. The grain is then measured precisely and ground to uniform particle size. This insures consistency in the cooking and drying steps, and optimal water, heat and enzyme penetration without contributing to the difficulty of separation from the liquor. Grain ground to a substantially uniform size to pass through a 0.25 millimeter screen (60 mesh) is believed to be preferred. If desired, grain bran also may be added to supplement the fiber content of the final product. It is understood that this milled grain may consist of wheat, corn, pearled barley, psyllium, millet, rice, rye, sorghum, oats, or other starch-bearing grain, either alone or in combination, without departing from the process of the present invention.

The milled grain or grains is slurried with a selected amount of water in a cooking vessel and then vigorously agitated to produce a completely homogeneous slurry. A homogeneous mixture insures that the particles of milled grain in the slurry are heated uniformly and have optimal contact with the water. This slurry typically has a solids content between 20 to 50 percent to ultimately produce a convenient concentration of sugar in the liquid portion.

The slurry is then heated by a conventional means, such as steam injection, to the gelatinization temperature of the selected grain. Although gelatinization temperatures will vary from grain to grain, the gelatinization temperature of typical grains ranges from 60 to 77 degrees C. Although complete gelatinization is preferred, partial gelatinization is acceptable. However, it should be understood that partial gelatinization greatly increases the amount of time required for conversion of the selected amount of starch.

As the grain slurry approaches the gelatinization temperature, the solid starch granules begin to swell. This swelling breaks apart the structure of the starch and forms an unstable suspension of high molecular weight glucose polymers, which are now exposed to breakdown by enzymatic action. At this point, the slurry has thickened considerably and is ready for hydrolysis.

Preferably, one or more alpha-amylase enzymes is used for liquifying and converting the starch to sugars. These enzymes act to break down the long glucose polymer chains, which make up the starch, into shorter molecular chains called dextrins. Once a glucosyl bond is broken, the alpha amylase is released and is available to repeat the process with other long glucose chains yet unbroken. Repeated hydrolysis of the glucose polymer chain at different points breaks the starch into smaller and smaller dextrin chains. Accordingly, if conditions remained favorable and enough time were allowed, many of the glucose polymer chains would be broken into individual glucose molecules.

For the purpose of the present invention, such extensive breakdown is undesirable. A high amount of glucose relative to total dextrins produces stickiness, excessive nitrogen-free extract, drying difficulties, and an undesired darker color in the final grain product. Proper selection of enzymes can adequately promote the liquification of the starch without excessive glucose formation. In contrast, the alcohol production processes of the prior art actively promote the complete hydrolysis of the starch to glucose. It is preferred in the present invention that the percent of glucose in the sugars remains low; preferably below 5%, and more preferably below 1%.

It is preferred that the selected enzyme be added before the gelatinization temperature of the grain is reached to insure thorough mixing, but it is understood that the enzyme may be added at any time. Many enzymes which are well known in the art are believed acceptable for starch liquification and conversion in the above process including alpha amylases, proteases, pectinases and amyloglucosidases. A particularly suitable enzyme is a bacterial alpha-amylase available from Alltech, Inc. of Lexington, Ky. and sold under the trademark DEX-ZYME.

A useful characteristic of enzymes is that their activity is extremely temperature sensitive. Below a certain temperature they are substantially inactive. Above a higher temperature they are irreversibly destroyed.

Once the selected enzymes have been added according to manufacturer's instructions and the gelatinization temperature is reached, the heating is temporarily halted and the degradation of starch is allowed to progress. Because of the thickening of the slurry, it is recommended that vigorous agitation be applied throughout the starch removal process. The preferred temperature range of the slurry during hydrolysis is from 75 degrees C. to 88 degrees C.

It is a feature of the present invention that substantially all (90 to 100%) of the starch be hydrolyzed, but preferably the enzymatic action should be halted before the quantity of glucose molecules exceeds a range of 1% to 5%. The progress of the degradation of the starch may be monitored by several simple methods, alone or, more preferably, in combination. These tests are the conventional starch-iodine test and the Brix specific gravity test for measuring sugar concentration. Although other factors can influence the Brix value, for simplicity the Brix value is considered equal to percent sugar.

The starch-iodine test is a procedure to determine the presence of raw starch in the cooked grain slurry. Five or six drops of stock potassium iodide and iodine solution is added to a test tube with water. Two or three milliliters of the slurry to be tested is added to this solution. After shaking, a blue color indicates the presence of starch. Accordingly, the absence of any bluish tint indicates complete starch conversion.

The Brix test is a measure of dissolved solids in solution. These dissolved solids may include proteins and inorganic salts, but are predominantly mono-, di-, tri-, and poly-saccharides. There is no simple method for quantifying these sugars, but the Brix test offers a qualitative check on the amount of sugars solubilized through this stage of the process. Brix may be measured with a Brix, Balling, or specific gravity hydrometer, or a temperature compensating refractometer.

The preferred enzymes are those which break down the long starch polymers quickly but do not excessively promote the formation of glucose molecules. The cessation of enzymatic activity before excessive glucose molecules are produced is easily accomplished by several alternative methods. One method entails destroying the enzyme once the slurry tests at the selected level of starch conversion. This irreversible destruction of the enzyme is affected by heating the slurry very rapidly to a temperature above the maximum temperature tolerance level of the enzyme or "kill-point." This temperature varies from enzyme to enzyme, but it is preferred that the selected enzyme have a narrow activity range for easy destruction. Typically, this temperature may be between 88 degrees C. to 99 degrees C. In an alternative method, the hydrolysis may be arrested by quickly separating the grain from the slurry and drying. Other methods of inactivating the enzyme include alteration of pH, chemical destruction and other methods known to those skilled in the art.

Once the necessary temperature is obtained to inactivate the enzyme, the slurry is much less viscous. No matter how the enzyme is inactivated, it is a critical feature of the present invention that the grain solids are separated from the aqueous sugar fraction before fermentation. Contrary to the prior art, it is extremely important that no part of the prospective food product ever be subjected to the fermentation process.

The grain solids consist of insoluble protein portions of the grain, fiber and, optionally, a small amount of unconverted starch. The aqueous liquid consists of the soluble portion of the grain including some proteins and sugars, (i.e. the higher dextrins and glucose) that have just been obtained from the hydrolysis of the starch. Typically, these sugars are composed of 99% higher dextrins and less than 1% glucose.

As mentioned earlier, the amount of starch selected to be removed is between 90 to 100%. In some embodiments of the present invention, it may be desired to leave some starch in the grains to aid in the drying process. Naturally, if this is done, the relative amount of protein and fiber will be proportionately reduced. Accordingly, the least amount of residual starch necessary for drying enhancement is preferred. A removal of 98% of the starch is adequate for most purposes so it is therefore most preferred.

In other embodiments of the present invention complete removal of starch is preferred. Accordingly, it has been found preferred that the hydrolysis should be stopped as quickly as possible after the cooked slurry tests "starch negative" using the starch-iodine test. This "starch negative" point is defined as 100% removal of starch. Again, the hydrolysis of larger dextrins into glucose continues after the "starch negative" point is reached, so the arresting of hydrolysis is preferred before the amount of glucose reaches 5% of the total sugar.

The grain solids may be removed from the aqueous sugar fraction by any conventional method, but centrifugation has been found particularly desirable to form the solids cake. This solids cake contains the fiber and protein plus a certain amount of dextrins retained in the liquid with the solids. However, it is understood that too much dextrins retained in the solids will proportionately lower the protein and fiber content of the finished product. A preferred amount of sugars remaining on the solids product after drying is between 4 to 30% by weight on a dry basis. A preferred level of nitrogen-free extract on a dry weight basis is less than 40%, with less than 30% more preferred and less than 20% most preferred.

One of the reasons centrifugation has been found particularly desirable is that the residual sugar content may be easily controlled. Typically, the solids are removed from the centrifuge as a pumpable solids cake having about 30 to 50% solids, which means that 50 to 70% of the solids cake is sugar water having a sugar concentration between 5 and 24%. Therefore, it is understood that the sugar content of the final product will vary not only with the sugar content of the aqueous fraction but also by the selected solids content of the solids cake. Although a sugar content between 5 to 24% is acceptable, it may be preferred to select a water to grain ratio to produce a sugar content of 11 to 20%. To conveniently produce a product having a nitrogen-free extract of less than 40% when the starch is 100% hydrolyzed, a sugar content of 15 to 17% is more preferred.

Residual sugar is an important feature of the present invention and should be controlled to maintain the residual sugar content of the final product above 4%. Sugar contents substantially above 30% result in unnecessary caloric content, reduced relative protein and fiber content, and drying problems. Accordingly, the residual sugar content of the final product should be between 4 to 30% with 4 to 18% more preferred and 7 to 11% most preferred.

It is modern convention to characterize grain products by measuring the content of protein, total dietary fiber, ash, fat and nitrogen-free extract, as a weight percent on a dry matter basis. The nitrogen-free extract includes total sugars, starches and everything not accounted for in the other catagories. This is calculated by subtraction and is sometimes reported as "carbohydrates." Accordingly, for convenience and conformity, residual sugar, and unconverted residual starch if any, are combined and reported as nitrogen-free extract. When residual sugar values are reported, the value is calculated by a suitable method, such as mass balance, and does not include any starch.

In order to maintain the desirable characteristics of the product of the present invention, the drying process should be carefully monitored to prevent scorching or discoloration. Accordingly, the cake should be dried quickly and at the lowest convenient temperature, preferably not to exceed 75 degrees C.

The amount of moisture remaining in the dried product can affect the color and shelf life of the product. A moisture content below 10% is preferred in order to prevent the onset of mold in storage. However, it is inconvenient to reduce the moisture level substantially below 2% because of the residual sugar coating. Accordingly, a moisture content between 2 to 10% is desired with 4 to 8% more preferred.

The cake may be dried by any appropriate low-temperature dehydration process, such as drum dryers, flash dryers, spray dryers, or the like. The texture of the final product is affected by the drying process, with a flake usually preferred over a granule. Spray dryers tend to produce granules, while drum dryers have proven to be particularly desirable for a flake-like final product.

It should be noted that the process of the present invention results in the enzymatically reduced grain being coated or encapsulated by the residual sugars. This coating, together with the cooking and degradation process described earlier, acts to smooth the otherwise rough and jagged particles to enhance the "mouthfeel" of the product and overcome the unpleasant coarseness heretofore associated with bran products. Further, the coating acts to isolate the tongue from the bran thereby reducing the harshness of the bran flavor. It should be remembered that the residual augars of the coating are particularly rich in less sweet, higher dextrins relative to the sweeter glucose and therefore does not promote an inappropriate oversweetness in the finished product.

The solids-free aqueous sugar fraction from the above separation has a sugar content as indicated by Brix value to be approximately 5 to 24%. For efficient alcohol production, a sugar content of 16 to 24% is preferred. This aqueous sugar fraction, or sweet wort, is now pumped to an appropriate vessel and a thermostable alpha-amylase, such as ALLCOHOLASE HIGH T (Alltech, Inc. Lexington, Ky.) is added and the aqueous sugar solution is heated to 88 to 93 degrees C. This enzyme addition with heating will hydrolyze the higher dextrins and any unconverted starch to produce a minimum of 3 to 5% glucose in the sugar fraction which is preferred for initial fermentation. The sweet wort is held at this temperature for approximately one hour. In the alternative, the aqueous sugar fraction may be cooled and pumped directly to the fermenters, although this is not preferred.

Following the pre-fermentation heating and holding period, the solids-free aqueous sugar fraction may now be transferred to the fermenter. The sugar fraction is first cooled to a temperature of 32 degrees C. It is typically innoculated with: (a) penicillin; (b) 0.02 to 0.03% amyloglucosidase enzyme such as ALLCOHOLASE II (Alltech); (c) yeast; and (d) yeast nutrients. The fermentation step is carried to completion in a conventional manner over a period of 24 to 48 hours. The alcohol is removed from the fermentation beer by distillation to produce substantially pure (95%) grain alcohol. The stillage from this distillation contains yeast cells and any unfermented solubles contained in the aqueous sugar fraction. The yeast cells are particularly high in by-pass proteins and make a valuable cattle feed ingredient when combined with low-quality roughage.

EXAMPLE ONE

Number 2 red wheat was ground in a hammermill with a 3.175 millimeter screen. One thousand eight hundred sixteen kilograms of this milled grain was added to 7,000 liters of water at 20 degrees C. and stirred. This produced a grain slurry having a solids content of 21% by weight. According to manufacturer's instructions, calcium in the form of 1.4 kilograms of food-grade lime was added to the water to provide a free calcium ion to enhance the viability of the enzyme. The slurry was heated by direct steam injection until a temperature of 27 degrees C. was obtained and 2.7 kilograms of DEX-ZYME was added (0.15% by weight of the grain used).

Heating with stirring was continued until a temperature of 82 degrees C. was obtained and the slurry was maintained at that temperature for approximately 24 minutes. A conventional starch iodine test indicated only a slight presence of starch in the slurry with a sugar content of 19.5% as determined by Brix value.

Steam was again injected into the slurry until the slurry reached a temperature of 93 degrees C. and the steam was shut off. This heating was sufficient to destroy the enzyme and arrest hydrolysis. A conventional starch-iodine test now indicated "starch negative" and a sugar content of 20.5% was measured. At this point, the slurry had an aqueous sugar fraction composed of 99.7% dextrins and 0.3% glucose.

The slurry was pumped to a Sharples P-3400 Solid Bowl centrifuge at a rate of approximately 57 liters per minute and centrifuged at approximately 4000 rpm. The solids cake from the centrifuge contained about 30 percent solids and was pumped to a double drum dryer for drying. The dried product had a moisture content of 5.7%. The color, taste, and texture were determined to be satisfactory. On a dry basis, the product had the following characteristics:

| | |
|---|---|
| Protein | 25.5% |
| Total Dietary Fiber (AOAC method) | 45.4% |
| Nitrogen Free Extract | 23.6% |
| Ash | 3.1% |
| Fat | 2.4% |
| Unconverted Starch | None Detected |

EXAMPLE TWO

Wheat was milled in a hammermill with a 3.175 millimeter screen and 1544 kilograms was added to water at 21 degrees C. Two hundred and seventy two kilograms of oat groats were similarly ground and added to the wheat and water slurry to produce a slurry having approximately 21% solids, of which 85% was wheat and 15% was oats. No calcium was added to aid hydrolysis. The slurry was heated with live steam to a temperature of 49 degrees C. and 2.7 kilograms of DEX-ZYME (0.15% by weight of grain) was added. Heating was continued to 82 degrees C. over a period of 37 minutes and the steam injection was stopped. At this point, a conventional starch iodine test indicated only a slight presence of starch with a sugar content of 18%. This indicated approximately 99% of the starch was converted. The slurry was held at 82 degrees C. for fifteen minutes and thereafter pumped to the centrifuge for the separation of solids. The solids cake, being again approximately 30% solids, was pumped to a double drum dryer for drying.

It should be noted that the hydrolyzing enzyme was not taken to the "kill-point" by heating above 93 degrees C. Instead, the grains were separated and dried to 2.7% moisture to arrest hydrolysis while a presence of starch was indicated. Consequently, the starch content was significantly higher than the product of Example One.

The product on a dry matter basis was characterized as follows:

| | |
|---|---|
| Protein | 20.3% |
| Total Dietary Fiber (AOAC method) | 47.8% |
| Nitrogen Free Extract | 26.4% |
| Ash | 3.1% |
| Fat | 2.4% |
| Soluble Dietary Fiber | 9.4% |

It should be noted that the "carbohydrates" or nitrogen-free extract measure includes both unconverted starch and residual sugars. Because of the higher carbohydrate content, the protein was lower. The color of the product was somewhat lighter (more tan) than the all-wheat product with a slightly different, yet pleasing, taste due to the presence of the oats. The texture of the oat-wheat product was substantially the same in baking tests. It should be particularly noted that this product contains a desirable balance of soluble fiber to insoluble fiber.

EXAMPLE THREE

Two thousand seven hundred and twenty four kilograms of degermed whole wheat flour was added to 8,024 liters of water in a large cooker and stirred. This produced a grain slurry having a solids content of approximately 25%. Contrary to enzyme manufacturer's instructions, no calcium was added to the water. The absence of additional free calcium makes the enzyme easier to destroy after hydrolysis has taken place. The agitated slurry was heated over a 30 minute period by direct steam injection until a temperature of 38 degrees C. was obtained and thereafter 2.7 kilograms of DEX-ZYME was added (0.1% by weight of flour).

Heating with stirring was continued for a period of 30 minutes until a temperature of 96 degrees C. was obtained. At this point, the slurry was just "starch negative" and the sugar content was approximately 16%±1%. After the desired temperature was reached, the injection of steam was reduced and held at 96 degrees C. for 15 minutes to completely destroy the enzyme.

The slurry was transferred to a holding tank for storage until it was convenient to separate the solids. When convenient, the slurry was pumped to a Bird HB-1400 centrifuge at a rate of approximately 125 liters per minute and centrifuged at 3600 rpm at 85 degrees C. The solids cake from the centrifuge contained about 40% solids. The solids cake was dried as in Example 1 and on a dry basis had the following average characteristics:

| | |
|---|---|
| Protein | 27.0% |
| Total Dietary Fiber (AOAC method) | 40.8% |
| Nitrogen Free Extract | 25.2% |
| Ash | 4.5% |
| Fat | 2.5% |
| Unconverted Starch | None detected |

In order to provide for helpful comparisons between the reported analyses of the present invention and published analyses of grain products of some of the prior art, some explanations may be useful. Until recently, fiber was often reported as "crude" fiber (AOAC method 7.071). Fiber analysis of the present invention uses the more modern total dietary fiber (AOAC method). Analysis of the same sample by the two different methods may result in a total dietary fiber a magnitude of 3 to 4 times higher than "crude" fiber.

A way to correlate test results that can provide indirect comparisons utilizes the calculated measure of nitrogen-free extract. The percentages of water, ash, protein, fiber and fat are simply added together and the sum subtracted from 100 percent. Since nitrogen-free extract is a calculated number consisting of the remainder of constituents after other analyses have been made, it can be useful in comparing crude fiber to total dietary fiber. If all other analyses are the same, the increase in crude fiber related to total dietary fiber is reflected in a percentage decrease in nitrogen-free extract. For example, the results of the same corn DDGS sample analysis using two different fiber methods are set forth below:

| GRAIN | ASH | FAT | PROTEIN | | NITROGEN-FREE EXTRACT |
|---|---|---|---|---|---|
| | | | | CRUDE FIBER | |
| Corn DDGS | 10.1% | 9.0% | 23.0% | 6.3% | 51.6% |
| | | | | TOTAL DIETARY FIBER | |
| Corn DDGS | 10.1% | 9.0% | 23.0% | 32.0% | 25.9% |

It may be seen that the sum of crude fiber and nitrogen-free extract is the same as the sum of total dietary fiber and nitrogen-free extract. Therefore, because of the conventional and consistent use of nitrogen-free extract when reporting analyses, correlations between fiber measuring methods can easily be made.

As discussed previously, many starch-bearing grains may be used in the process, and made into products of the present invention. Inasmuch as the specific characteristics of the finished products depend greatly on the selected whole grain, degree of hydrolysis, and the selected amount of water in the grain slurry, the following tables set forth theoretical estimated product characteristics for selected process variables within the scope of the present invention. The following examples assume that the water to grain ratio is constant and as described in Example One. The grain solids content from the centrifuge is assumed to be 30 to 50% by weight.

When wheat is the grain of choice, the anticipated preferred characteristics would be fiber content substantially between 30 and 70%, protein content substantially between 17 to 35% and nitrogen-free extract content substantially between 20 to 40%, all by weight.

When a mixture of wheat and oats is the grain- of choice, the anticipated preferred characteristics would be fiber content substantially between 40 to 55%, protein content substantially between 20 to 30% and nitrogen-free extract substantially between 20 to 40%, all by weight. If desired, the ratio of wheat to oats could be adjusted to produce a product having a mixture of 20% soluble fiber and 80% insoluble fiber.

When rice is the grain of choice, the anticipated preferred characteristics would be fiber content substantially between 40 to 45%, protein content substantially between 17 to 23%, and nitrogen-free extract substantially between 30 to 40%, all by weight.

When corn is the grain of choice, the anticipated preferred characteristics would be fiber content substantially between 40 to 46%, protein content substantially between 20 to 25%, and nitrogen-free extract substantially between 20 to 30%, all by weight.

TABLE I

| | ESTIMATE AT 90% HYDROLYSIS | | | | |
|---|---|---|---|---|---|
| GRAIN | NITROGEN FREE EXTRACT (NFE) | TOTAL DIETARY FIBER | TOTAL OF NFE AND FIBER | RESIDUAL SUGAR | PROTEIN |
| Rice | 33.5% | 41.0% | 74.5% | 23.5% | 20.5% |
| Wheat | 27.0% | 45.0% | 72.0% | 17.0% | 23.0% |
| Corn | 29.1% | 43.9% | 73.0% | 19.1% | 22.0% |
| Wheat/Oats | 27.7% | 44.8% | 72.5% | 17.7% | 22.5% |

TABLE II

| | ESTIMATE AT 98% HYDROLYSIS | | | | |
|---|---|---|---|---|---|
| GRAIN | NITROGEN FREE EXTRACT (NFE) | TOTAL DIETARY FIBER | TOTAL OF NFE AND FIBER | RESIDUAL SUGAR | PROTEIN |
| Rice | 30.5% | 43.0% | 73.5% | 28.5% | 21.5% |
| Wheat | 24.6% | 46.9% | 71.5% | 22.6% | 23.5% |
| Corn | 27.0% | 45.3% | 72.3% | 25.0% | 22.7% |
| Wheat/Oats | 22.9% | 48.0% | 70.9% | 20.9% | 24.1% |

TABLE III

| | ESTIMATE AT 100% HYDROLYSIS | | | | |
|---|---|---|---|---|---|
| GRAIN | NITROGEN FREE EXTRACT (NFE) | DIETARY FIBER | TOTAL OF NFE AND FIBER | RESIDUAL SUGAR | PROTEIN |
| Rice | 30.0% | 43.3% | 73.3% | 30.0% | 21.7% |
| Wheat | 23.6% | 47.5% | 71.1% | 23.6% | 23.9% |
| Corn | 26.1% | 45.7% | 71.8% | 26.1% | 23.2% |
| Wheat/Oats | 21.8% | 48.7% | 70.5% | 21.8% | 24.5% |

For comparison purposes, some of the grain products of the prior art are set forth in Table IV.

TABLE IV

| | NITROGEN FREE EXTRACT (NFE) | CRUDE FIBER | TOTAL OF NFE AND FIBER | PROTEIN |
|---|---|---|---|---|
| DISTILLER'S DRIED GRAINS | | | | |
| Corn | 45.9% | 9.9% | 55.8% | 28.6% |
| Rye | 52.3% | 12.5% | 64.8% | 26.4% |
| Wheat | 45.1% | 13.9% | 59.0% | 30.6% |
| BREWER'S SPENT GRAINS | | | | |
| Barley | 47.9% | 19.9% | 67.8% | 21.9% |
| RASCO PATENT #4,828,846 | | | | |
| Wheat DDGS | 49.9% | 6.8% | 56.7% | 33.9% |
| Corn DDGS | 51.5% | 6.3% | 57.8% | 23.0% |

The food product of the present invention is organoleptically suitable for wide spread use in human foods, particularly as a component in baked goods, fried sweet goods, cereals (cooked or ready-to-eat), diet supplements, meat extenders, salad toppings, granola bars, yogurt, and snack foods without the requirement of reformulation. Baked goods include items such as breads, rolls, pancakes, muffins, cakes, cookies, tortillas, pastas and noodles. In baking tests, products of the present invention have been substituted for flour in baked goods between 20 to 50% without loss of consumer acceptability. Bran muffins have been made at 100% substitution of flour with the product of the present invention with only minimal loss of acceptability.

From the foregoing, it would be appreciated that although specific embodiments of the invention have been described herein for purposes of illustration, various modifications may be made without deviating from the spirit and scope of the invention.

We claim:

1. A high fiber, high protein food product organoleptically suitable for human consumption comprising:
   milled, starch-bearing cereal grains having 90 to 100% of the starch enzymatically converted, said converted cereal grains having a protein content on a dry matter basis substantially between 17 to 35% by weight, a total dietary fiber content on a dry matter basis substantially between 30 to 70% by weight and a nitrogen-free extract content on a dry matter basis of less than 40% by weight, said converted grains having a coating thereon of residual sugars from the enzymatic conversion of starch substantially between 4 to 30% by weight on a dry matter basis, the residual sugars containing less than 5% glucose.

2. The food product of claim 1 wherein the nitrogen-free extract content is less than 30% by weight.

3. The food product of claim 2 wherein the nitrogen-free extract content is less than 20% by weight.

4. The food product of claim 1 wherein the residual sugars are substantially between 7 to 11% by weight.

5. The food product of claim 1 wherein the total dietary fiber content is substantially between 40 to 55% by weight.

6. The food product of claim 1 wherein the cereal grains are selected from the group consisting of wheat, oats, rice, corn, psyllium, millet, rye, pearled barley, sorghum, and mixtures thereof.

7. The food product of claim 6 wherein the cereal grain is wheat and the fiber content is substantially between 40 to 55% by weight, the residual sugars coating content is substantially between 7 to 11% by weight and the nitrogen-free extract content is substantially between 20 to 30% by weight.

8. The food product of claim 6 wherein the cereal grain is a mixture of wheat and oats, the fiber content is substantially between 40 to 55% by weight, the protein content is substantially between 20 to 30% by weight and the nitrogen-free extract is substantially between 20 to 30% by weight.

9. The food product of claim 6 wherein the cereal grain is rice, the fiber content is substantially between 40 to 45% by weight, the protein content is substantially between 17 to 23% by weight and the nitrogen-free extract is substantially between 30 to 40% by weight.

10. The food product of claim 6 wherein the cereal grain is corn, the fiber content is substantially between 40 to 46% by weight, the protein content is substantially between 20 to 25% by weight and the nitrogen-free extract is substantially between 20 to 30% by weight.

11. The food product of claim 8 wherein the fiber content is a selected mixture of soluble fiber and insoluble fiber.

12. A process for producing a high protein, high fiber food product organoleptically suitable for human consumption from selected starch-bearing cereal grains comprising the steps of:
   suspending starch-bearing cereal grains in a selected amount of water to form an aqueous slurry;
   heating the slurry sufficiently to at least partially gelatinize the starch;
   liquifying and hydrolyzing a selected amount between 90 to 100% of the starch in the grains with enzymes to produce a grain mixture having a grain solids fraction and an aqueous sugars fraction with a selected sugars content substantially between 5 to 24%, the sugars of the sugars fraction containing less than 5% glucose; and
   separating the grain solids fraction of the mixture from the aqueous sugars fraction of the mixture to produce a substantially solids-free aqueous sugars fraction and a grain solids cake with a solids content substantially between 30 to 50% by weight and 50 to 70% aqueous sugars fraction by weight, said grain solids cake having a total dietary fiber content on a dry matter basis substantially between 30 to 70% by weight, a protein content on a dry basis substantially between 17 to 35% and a nitrogen-free extract content on a dry basis of less than 40% by weight.

13. The process of claim 12 wherein the hydrolysis of the starch is irreversibly arrested before separating the grain solids by elevating the temperature of the grain mixture to a selected temperature above the maximum temperature tolerance level of the liquifying enzymes.

14. The process of claim 12 wherein the selected amount of the liquified starch in the grains is between 90 to 98% and the hydrolysis of the starch is arrested by separating the grain solids fraction from the aqueous sugars fraction to form a solids cake and drying the solids cake to a moisture content of less than about 10% by weight.

15. The process of claim 13 wherein the selected temperature above the maximum temperature tolerance level of the liquifying enzymes is substantially between 88 degrees to 99 degrees C.

16. The process of claim 13 wherein the selected amount of hydrolyzed starch is 100% and the selected amount of water is sufficient to produce an aqueous sugars fraction having a sugar content substantially between 11 to 20% to produce a nitrogen-free extract content less than 30%.

17. The process of claim 13 wherein the cereal grain is wheat and the separating of grain solids fraction from aqueous sugars fraction includes centrifuging the grain mixture to produce a solids cake having a solids content between 30 to 50% by weight.

18. The process of claim 17 wherein the aqueous sugars fraction has a sugars content substantially between 11 to 20% and a fraction of glucose to total sugars of less than substantially 1%.

19. The process of claim 13 wherein the cereal grains are selected from the group consisting of wheat, oats, corn, rice, psyllium, millet, rye, pearled barley, sorghum and mixtures thereof.

20. The process of claim 19 wherein the cereal is wheat, the aqueous slurry has a solids content between 20 to 30% by weight, the hydrolysis is irreversibly arrested by heating to a temperature above 88 degrees C. when the selected amount of hydrolyzed starch is substantially 100%, the amount of glucose to total sugars is less than substantially 1% by weight, and the aqueous sugars fraction has a sugars content between 11 to 20%.

21. The process of claim 20 wherein the separation of grain solids from the aqueous sugars fraction includes centrifuging the grain mixture to produce a solids cake having a solids content between 30 to 50% by weight; and drying the solids cake to produce a food product having a nitrogen-free extract content less than 30% by weight on a dry basis, a total dietary fiber content greater than 40% by weight on a dry basis and a protein content substantially between 25 to 35% by weight on a dry basis.

22. The process of claim 13 wherein the selected grain is wheat, the selected amount of the liquified starch is substantially between 90 to 98% by weight, and the separating of the grain solids fraction from the aqueous sugars fraction includes centrifuging the grain mixture to produce a solids cake having a solids content between 30 to 50% by weight, including the step of;

drying the solids cake to produce a food product having a protein content of substantially 15 to 35% by weight on a dry basis, a total dietary fiber content between 40 to 55% by weight on a dry basis and a nitrogen-free extract content substantially between 30 to 40% by weight on a dry basis.

23. The process of claim 19 wherein the selected grain includes a mixture of wheat and oats to produce a food product having a mixture of soluble dietary fiber and insoluble dietary fiber.

24. The process of claim 12 further comprising the steps of:

fermenting the solids-free sugar fraction to produce an ethanol containing liquor; and distilling the liquor to recover substantially pure ethanol.

25. The process of claim 24 further comprising the step of:

enzymatically hydrolyzing the solids-free sugars fraction to at least partially degrade the higher sugars in the sugar fraction to glucose before fermenting the solids-free sugar fraction.

26. A food product made by the process of claim 12.
27. A food product made by the process of claim 16.
28. A food product made by the process of claim 20.
29. A process for producing a high protein, high fiber food product organoleptically suitable for human consumption from selected starch-bearing cereal grains comprising the steps of:

suspending starch-bearing cereal grains in a selected amount of water to form an aqueous slurry;

heating the slurry sufficiently to at least partially gelatinize the starch;

liquefying and hydrolyzing a selected amount between 90 to 100% of the starch in the grains with enzymes to produce a grain mixture having a grain solids fraction and an aqueous sugars fraction with a selected sugars content, the sugars of the sugars fraction containing less than 5% glucose, separating the grain solids fraction of the mixture from the aqueous sugars fraction of the mixture to produce a substantially solids-free aqueous sugars fraction and a grain solids cake, drying the grain solids cake in the presence of sufficient quantity of the aqueous sugars fraction to produce a food product having a coating thereon of residual sugars from the enzymatic conversion of starch substantially between 4 to 30% by weight on a dry matter basis.

30. The process of claim 29 wherein the selected sugars content of the aqueous sugars fraction is substantially between 5 to 24% by weight.

31. The process of claim 30 wherein the selected sugars content of the aqueous sugars fraction is substantially between 11 to 20% by weight.

32. The process of claim 29 wherein the starch bearing cereal grain is wheat and said grain solids cake has a total dietary fiber content on a dry matter basis substantially between 30 to 70%, a protein content on a dry matter basis substantially between 17 to 35% and a nitrogen-free extract content on a dry matter basis of less than 40% by weight.

33. The process of claim 29 wherein the coating of residual sugars is substantially between 4 to 18%.

34. The process of claim 33 wherein the coating of residual sugars is substantially between 7 to 11%.

35. The process of claim 29 wherein the hydrolysis of the starch is irreversibly arrested before separating the grain solids by elevating the temperature of the grain mixture to a selected temperature above the maximum temperature tolerance level of the liquefying enzymes.

36. The process of claim 32 wherein the selected amount of starch is substantially 100% and the selected amount of water is sufficient to produce an aqueous sugars fraction having a sugar concentration substantially between 11 to 20% to produce a nitrogen-free extract content less than 30%.

37. The process of claim 35 wherein the selected amount of hydrolyzed starch is substantially 100% and the coating of residual sugars is substantially between 4 to 18%, the cereal grain is wheat and the dried grain solids cake has a dietary fiber content on a dry matter basis substantially between 40 to 55%, a protein content substantially between 25 to 35% and a nitrogen-free extract content of substantially between 20 to 40%.

38. The process of claim 29 wherein the cereal grains are selected from the group consisting of wheat, oats, corn, rice, psyllium, millet, rye, pearled barley, sorghum and mixtures thereof.

39. The process of claim 29 including adding grain bran to the starch-bearing cereal grain to supplement the fiber content of the food product.

* * * * *